United States Patent
Agaoglu et al.

(10) Patent No.: US 10,802,585 B2
(45) Date of Patent: Oct. 13, 2020

(54) ELECTRONIC DEVICES WITH DISPLAY OPERATION BASED ON EYE ACTIVITY

(71) Applicant: Apple Inc., Cupertino, CA (US)

(72) Inventors: Mehmet N. Agaoglu, Cupertino, CA (US); Andrew B. Watson, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/443,214

(22) Filed: Jun. 17, 2019

(65) Prior Publication Data

US 2020/0019238 A1 Jan. 16, 2020

Related U.S. Application Data

(60) Provisional application No. 62/697,286, filed on Jul. 12, 2018.

(51) Int. Cl.
*G06F 3/01* (2006.01)
*G02B 27/01* (2006.01)
*G06F 1/3234* (2019.01)

(52) U.S. Cl.
CPC ......... *G06F 3/013* (2013.01); *G02B 27/0172* (2013.01); *G06F 1/3265* (2013.01); *G09G 2320/046* (2013.01)

(58) Field of Classification Search
None
See application file for complete search history.

(56) References Cited

U.S. PATENT DOCUMENTS

| | | | |
|---|---|---|---|
| 8,225,229 B2 | 7/2012 | Thorn et al. | |
| 8,687,840 B2 | 4/2014 | Singhar et al. | |
| 9,361,833 B2 | 6/2016 | Kamhi | |
| 9,378,695 B2 | 6/2016 | Kim et al. | |

(Continued)

FOREIGN PATENT DOCUMENTS

| | | |
|---|---|---|
| EP | 1847978 A2 | 10/2007 |
| EP | 3109689 A1 | 12/2016 |
| WO | 2017040214 A1 | 3/2017 |

OTHER PUBLICATIONS

Lang, Ben, Researchers Exploit Natural Quirk of Human Vision for Hidden Redirected Walking in VR, Apr. 27, 2018, [retrieved May 29, 2018]. Retrieved from the Internet <roadtovr.com/researchers-exploit-natural-quirk-of-human-vision-saccade-hidden-redirected-walking-vr-gtc-2018/>.

*Primary Examiner* — Aneeta Yodichkas
(74) *Attorney, Agent, or Firm* — Treyz Law Group, P.C.; G. Victor Treyz; David K. Cole

(57) ABSTRACT

An electronic device may have a display for displaying image content. Head-mounted support structures in the device may be used to support the display. The electronic device may have an eye monitoring system that detects eye saccades and eye blinks. Control circuitry in the electronic device may coordinate operation of the display with periods of suppressed visual sensitivity that are associated with the saccades and blinks. By making adjustments to display circuitry and image content during periods of suppressed visual sensitivity, potentially visually obtrusive changes to displayed images can be hidden from a user of the electronic device. Adjustments to display operation may help reduce burn-in effects, may help reduce power consumption, and may otherwise improve device performance.

19 Claims, 5 Drawing Sheets

(56) References Cited

U.S. PATENT DOCUMENTS

| | | | |
|---|---|---|---|
| 9,874,933 | B1 | 1/2018 | Carryer |
| 10,082,870 | B2 | 9/2018 | Thunström et al. |
| 10,229,540 | B2 | 3/2019 | Bavor, Jr. et al. |
| 10,255,874 | B2 | 4/2019 | Wang |
| 10,353,464 | B2 | 7/2019 | Skogo et al. |
| 10,359,631 | B2 | 7/2019 | Samec et al. |
| 2007/0046815 | A1 | 3/2007 | Lee |
| 2014/0092006 | A1 | 4/2014 | Boelter et al. |
| 2015/0029096 | A1 | 1/2015 | Ishihara |
| 2016/0035320 | A1 | 2/2016 | Yoon et al. |
| 2016/0131911 | A1 | 5/2016 | Border et al. |
| 2017/0255259 | A1 | 9/2017 | Mor |
| 2017/0285735 | A1* | 10/2017 | Young .................. G06F 3/013 |
| 2017/0285736 | A1 | 10/2017 | Young et al. |

* cited by examiner

ELECTRONIC DEVICES WITH DISPLAY OPERATION BASED ON EYE ACTIVITY

This application claims the benefit of provisional patent application No. 62/697,286, filed Jul. 12, 2018, which is hereby incorporated by reference herein in its entirety.

BACKGROUND

This relates generally to electronic devices and, more particularly, to electronic devices with displays.

Electronic devices such as head-mounted devices and computers have displays. During operation of an electronic device, display adjustments may be made. For example, the brightness of a display may be adjusted.

Challenges can arise in making display adjustments during device operation. If care is not taken, display adjustments may be obtrusive to a user of an electronic device.

SUMMARY

An electronic device may have a display for displaying image content. The electronic device may be a head-mounted device or other electronic device. Head-mounted support structures may be provide in the device. The head-mounted support structures in the device may be used to support the display and other device components. An eye monitoring system may be supported by the head-mounted support structures.

The eye monitoring system may be used in detecting eye saccades and eye blinks of a user. The human retina is non-uniform in distribution of photoreceptors, and hence, visual acuity drops with distance from the retinal location with highest photoreceptor density, often referred to as the fovea. Saccades are fast, jerky, and mostly ballistic eye rotations. Humans make several saccadic eye movements per second to utilize this highest-resolution part of the retina to look at the object of interest. Blinks are brief closures of eyelids, fully or partially, to clean, moisten, and oxygenate the cornea. Blinking is a semi-automatic behavior, mostly done reflexively to avoid irritants, or routinely to spread the tear across the surface of the cornea. Humans blink many times per minute depending on various conditions.

During saccades and blinks, a user's visual sensitivity is temporarily suppressed. Control circuitry in the electronic device may take advantage of momentary suppression of the user's visual sensitivity to make adjustments to the operation of the display. For example, the control circuitry can coordinate operation of the display with periods of suppressed visual sensitivity that are associated with the saccades and blinks to reduce power consumption and/or to make potentially obtrusive image changes. By making adjustments during periods of suppressed visual sensitivity, these adjustments can be hidden from the user of the electronic device.

DETAILED DESCRIPTION

Electronic devices may be provided with displays. Sensors such as eye monitoring sensors may gather information on eye activity such as information on saccades and blinks. During operation of an electronic device, control circuitry in the electronic device may make display adjustments in coordination with periods of time that a user has decreased visual sensitivity. For example, display adjustments may be made during periods of suppressed visual sensitivity that are associated with eye blinks and saccades.

Electronic devices that include displays and eye monitoring systems may include, for example, head-mounted displays (e.g., head-mounted devices such as virtual reality or augmented reality glasses), cellular telephones, tablet computers, head-up displays in vehicles and other environments, laptop computers, desktop computers, televisions, wristwatches, and other suitable electronic equipment. In devices such as head-mounted displays, the general location of a user's eyes will be relatively constant during operation, facilitating accurate eye monitoring. In general, however, any suitable electronic device may be provided with an eye monitoring system (e.g., a stand-alone computer, a head-up display, a portable device, etc.).

Figure 1:
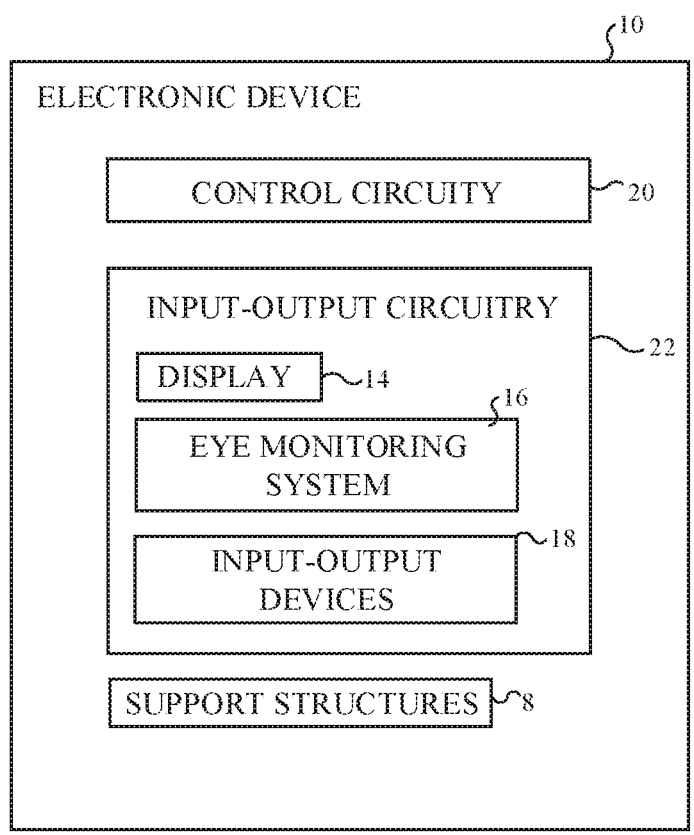
FIG. 1 is a schematic diagram of an illustrative electronic device such as a head-mounted display in accordance with an embodiment.

A schematic diagram of an illustrative electronic device with a display and an eye monitoring system is shown in FIG. 1. Electronic device 10 may be a head-mounted device (head-mounted display), a cellular telephone, a tablet computer, a head-up display, a laptop or desktop computer, a television, a wrist watch, or other electronic equipment. As shown in FIG. 1, electronic device 10 may have control circuitry 20. Control circuitry 20 may include storage and processing circuitry for controlling the operation of device 10. Circuitry 20 may include storage such as hard disk drive storage, nonvolatile memory (e.g., electrically-programmable-read-only memory configured to form a solid-state drive), volatile memory (e.g., static or dynamic random-access-memory), etc. Processing circuitry in control circuitry 20 may be based on one or more microprocessors, microcontrollers, digital signal processors, baseband processors, power management units, audio chips, graphics processing units, application specific integrated circuits, and other integrated circuits. Software code may be stored on storage in circuitry 20 and run on processing circuitry in circuitry 20 to implement control operations for device 10 (e.g., data gathering operations, operations involving the adjustment of display circuitry and other components using control signals, operations involved in processing eye activity data and data related to content being displayed for a user, etc.).

Device 10 may include input-output circuitry 22. Input-output circuitry 22 may be used to allow data to be received by device 10 from external equipment (e.g., a tethered computer, a portable device such as a handheld device or laptop computer, or other electrical equipment) and to allow a user to provide device 10 with user input. Input-output circuitry 22 may also be used to gather information on the environment in which device 10 is operating. Output components in circuitry 22 may allow device 10 to provide a user with output and may be used to communicate with external electrical equipment.

As shown in FIG. 1, input-output circuitry 22 may include a display such as display 14. Display 14 may be used to display images for a user of device 10. Display 14 may be an organic light-emitting diode display, a liquid crystal display, a liquid-crystal-on-silicon display, projectors or displays based on projecting light beams on a surface directly or indirectly through specialized optics, or any other suitable display. Display 14 may be used to present computer-generated content such as virtual reality content and mixed reality content to a user. Virtual reality content may be displayed in the absence of real-world content. Mixed reality content, which may sometimes be referred to as augmented reality content, may include computer-generated images that are overlaid on real-world images. The real-world images may be captured by a camera (e.g., a forward-facing camera) and merged with overlaid computer-generated content or an optical coupling system may be used to allow computer-generated content to be overlaid on top of real-world images. As an example, a pair of mixed reality glasses or other augmented reality head-mounted display may include a display device that provides images to a user through a beam splitter, prism, holographic coupler, or other optical coupler.

Input-output circuitry 22 may include an eye monitoring system such as eye monitoring system 16 for monitoring user eye activity. Using system 16, control circuitry 20 can detect eye activity such as saccades (rapid eye motions) and blinks (eyelid closures). System 16 may be a gaze tracking system and/or other circuitry that measures the point of gaze (direction of view) of the user's eyes and that monitors the position of the user's eyelids. Control circuitry 20 may detect saccades by monitoring the user's eyes for rapid eye movements with system 16. Blinks can be detected by observing the position and movement of the user's eyelids with system 16.

Eye monitoring system 16 may include image sensors, light sources, light detectors, optical components such as lenses, and/or other equipment to monitor the eyes of the user. System 16 may include, for example, one or more visible and/or infrared cameras that face a user's eyes and capture images of the user's eyes. During operation of device 10, control circuitry 20 may use system 16 to track a user's gaze and monitor for eye blinks. Cameras and/or other sensors in system 16 may, for example, determine the location of a user's eyes (e.g., the centers of the user's pupils) and may determine the direction in which the user's eyes are oriented (the direction of the user's gaze, sometimes referred to as a measured point of gaze). By processing this information and information on the location of display 14, the location of the user's point-of-gaze (sometimes referred to as the user's direction of view) and rapid motion of the user's eyes (e.g., changes in the user's point-of-gaze that are indicative of saccades) can be identified in real time. Eyelid status (e.g., eyelid position) can also be tracked with system 16 so that control circuitry 20 can determine the points in time at which a user's eyelid closes and opens.

User input and other information may be gathered using sensors and other input devices in input-output devices 18 (and, if desired, from eye monitoring system 16). Input-output devices 18 may include, for example, position and motion sensors (e.g., compasses, gyroscopes, accelerometers, and/or other devices for monitoring the location, orientation, and movement of device 10), may include force sensors, temperature sensors, touch sensors, buttons, capacitive proximity sensors, light-based proximity sensors, other proximity sensors, strain gauges, gas sensors, pressure sensors, moisture sensors, magnetic sensors, and other sensors, may include audio components such as microphones for gathering voice commands and other audio input, and may include speakers for providing audio output (e.g., for providing sound to the left and right ears of a user). If desired, input-output devices 18 may include haptic output devices (e.g., vibrating components), light-emitting diodes and other light sources, and other output components. Circuitry 22 may include wired and wireless communications circuitry that allows device 10 (e.g., control circuitry 50) to communicate with external equipment (e.g., remote controls, joysticks and other input controllers, portable electronic devices, computers, displays, etc.) and that allows signals to be conveyed between components (circuitry) at different locations in device 10.

Electronic device 10 may have housing structures (e.g., housing walls, etc.), as shown by illustrative support structures 8 of FIG. 1. In configurations in which electronic device 10 is a head-mounted device (e.g., a pair of glasses, goggles, a helmet, a hat, etc.), support structures 8 may include head-mounted support structures (e.g., a helmet housing, head straps, temples in a pair of eyeglasses, goggle housing structures, and/or other head-mounted structures). The head-mounted support structures may be configured to be worn on a head of a user during operation of device 10 and may support display 14, eye monitoring system 15, other input-output circuitry 22, and circuitry 20.

Figure 2:
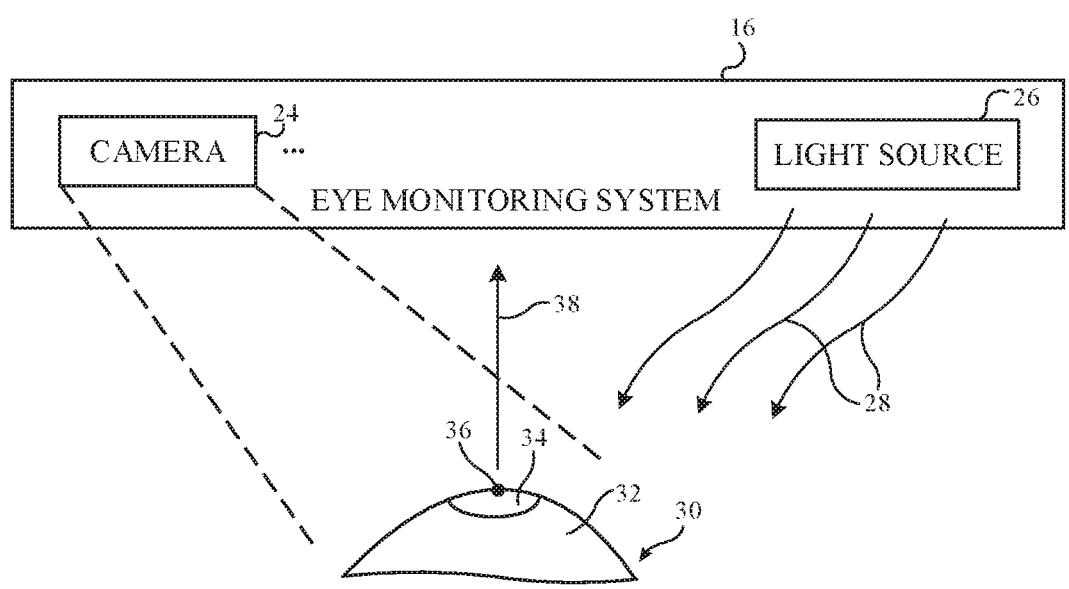
FIG. 2 is a top view of an illustrative eye monitoring system in accordance with an embodiment.

FIG. 2 is a diagram showing how eye monitoring system 16 may gather information on a user's eye 30. System 16 may, if desired, include gaze tracking system components such as light-emitting diodes, lasers, or other light sources, image sensors, photodetectors, and/or other light-sensing devices, and/or other equipment for monitoring eye movements and blinks. Eye tracking in system 16 may be performed by estimating the reflection of an infrared beam from the surface of the cornea ("corneal reflection"). If desired, system 16 may be a video-based eye tracker that uses the pupil center (without any reflection from the eye) to estimate gaze. System 16 may also use the fourth reflection from the inner (posterior) surface of the eye lens (sometimes referred to as Purkinje images). If desired, a three-dimensional geometric model of the eye may be constructed using more than one camera in system 16 that views the eye. This type of arrangement uses images of the eye to build a model, and then infers the orientation of the eye globe, i.e., the gaze, based on that model. In general, any of these approaches and/or other suitable approaches may be used for eye tracking in system 16.

As shown in FIG. 2, system 16 may, as an example, include one or more image sensors such as camera(s) 24. Each camera may be focused on the front of a user's eye such as eye 30 so that the characteristics of the user's eye can be measured. In some illustrative arrangements, one or more light-emitting diodes, lasers, lamps, and/or other light-emitting components may be used to form a light source for system 16 (see, e.g., light source 26).

During operation, light source 26 may emit light 28. For example, light source 26 may emit one or more beams of light 28 towards the user's eye 30 (e.g., 1-10 beams of light, at least 2 beams of light, at least 6 beams of light, 4-7 beams of light, 4-9 beams of light, etc.). Light 28 may be reflected off of the surface of eye 30. Camera 24 may gather images of eye 30. Information on the appearance of eye 30 (e.g., iris information, pupil information, blood vessel information, etc.) and/or information on reflected light (e.g., one or more light beams) from cornea 32 and other portions of eye 30 may be used by control circuitry 20 to determine the location of pupil center 36 of pupil 34 and the direction in which the user is currently gazing (gaze direction 38). The eye position information (pupil center information, eye orientation, etc.)

that is gathered by system 16 may be used by control circuitry 20 to identify saccades. Blinks can be measured by monitoring for the loss of a tracked eye position at the output of system 16, by using camera 24 to dynamically track eyelid position (e.g., eyelid height), and/or by otherwise viewing eye 30 to monitor for blinking. System 16 may detect, for example, closing movements of a user's eyelid and opening movements of a user's eyelid. In some configurations, saccade initiation and blink initiation times may be gathered. Saccade termination and/or blink termination information can also be gathered (e.g., so that saccade and/or blink durations may be determined). In general, any suitable eye tracking system may be used in monitoring a user's eyes. The eye tracking system arrangement of FIG. 2 is illustrative.

In response to gathered eye activity information (e.g., information on saccades and/or blinks), control circuitry 20 may make display system adjustments. For example, content that is being displayed on display 14 and/or operating characteristics of the circuitry associated with display 14 may be adjusted. A user's visual sensitivity is generally decreased temporarily during eye activity such as during saccades and during blinks. As a result, display adjustments that might otherwise be visible to a user and potentially obtrusive may go relatively unnoticed by a user if made during saccades and/or blinks. This approach allows device 10 to make adjustments to the operation of display 14 (including adjustments to the hardware of display 14 and adjustments to image data corresponding to image content being displayed on display 14) without creating undesired visual artifacts.

Figure 3:
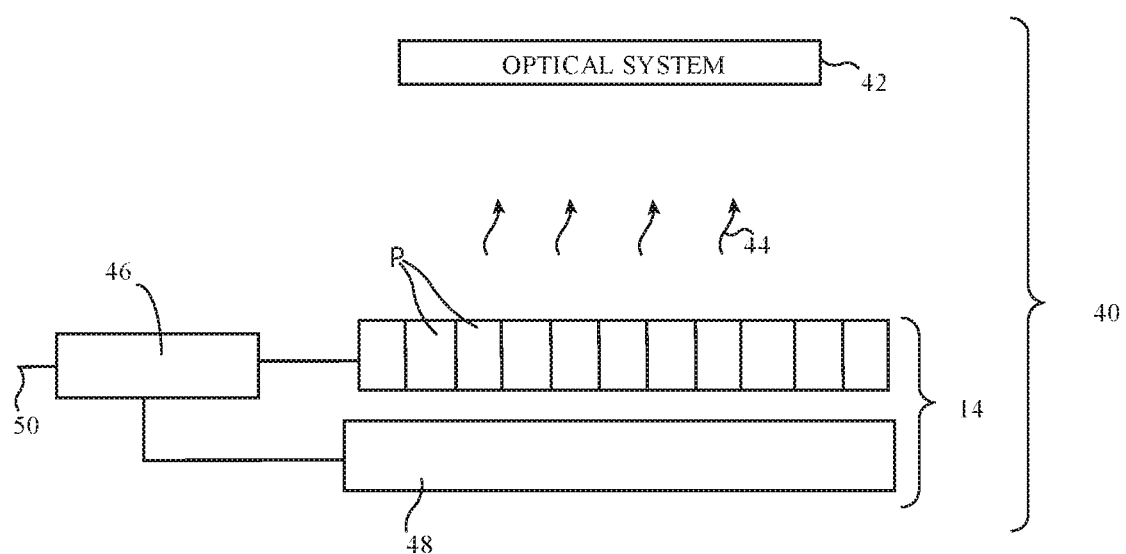
FIG. 3 is a diagram of an illustrative display system in accordance with an embodiment.

An illustrative display system is shown in FIG. 3. As shown in FIG. 3, display system 40 may include display 14. Display 14 may have an array of pixels such as pixels P that produce images (see, e.g., image light 44). Display circuitry 46, which may sometimes be referred to as control circuitry (see, e.g., control circuitry 20) may include display driver circuitry such as one or more timing controller integrated circuits (TCONs) and/or other processing circuitry for controlling the presentation of image content with pixels P. Display circuitry 46 may receive digital image data on input 50 and may issue timing control signals, data signals, gate signals, and/or other control and data signals to present content for a user with pixels P.

In some configurations, display 14 may include a separately adjustable illumination unit such as backlight unit 48 (e.g., in liquid crystal display systems in which pixels P are liquid crystal display pixels). In reflective display systems, unit 48 may supply illumination that is reflected off of a reflective display device (e.g., a liquid-crystal-on-silicon display device or a digital mirror device). During operation, control circuitry 20 may adjust the amount of output light from unit 48 (e.g., to adjust the brightness of images being presented by display 14). In other arrangements, the overall luminance of image content on pixels P may be adjusted by making global adjustments to the image data for pixels P (e.g., by reducing image luminance in the data being provided to an organic light-emitting diode display or a display having an array of micro-light-emitting diodes). Control circuitry 20 may also make electro-optical transfer function adjustments (gamma curve adjustments) and/or color cast adjustments to the image data corresponding to the images being displayed on display 14.

Image light 44 from display 14 may be provided to the eyes of a user using optical system 42. Optical system 42 may include beam splitters, prisms, holographic couplers, waveguides, lenses, mirrors, filters, and/or other components for routing image light to a user's eyes. Display system 40 of FIG. 3, eye monitoring system 16 of FIG. 2, control circuitry 20, and input-output circuitry 22 may be supported by support structures 8 (e.g., head-mounted support structures).

Figure 4:
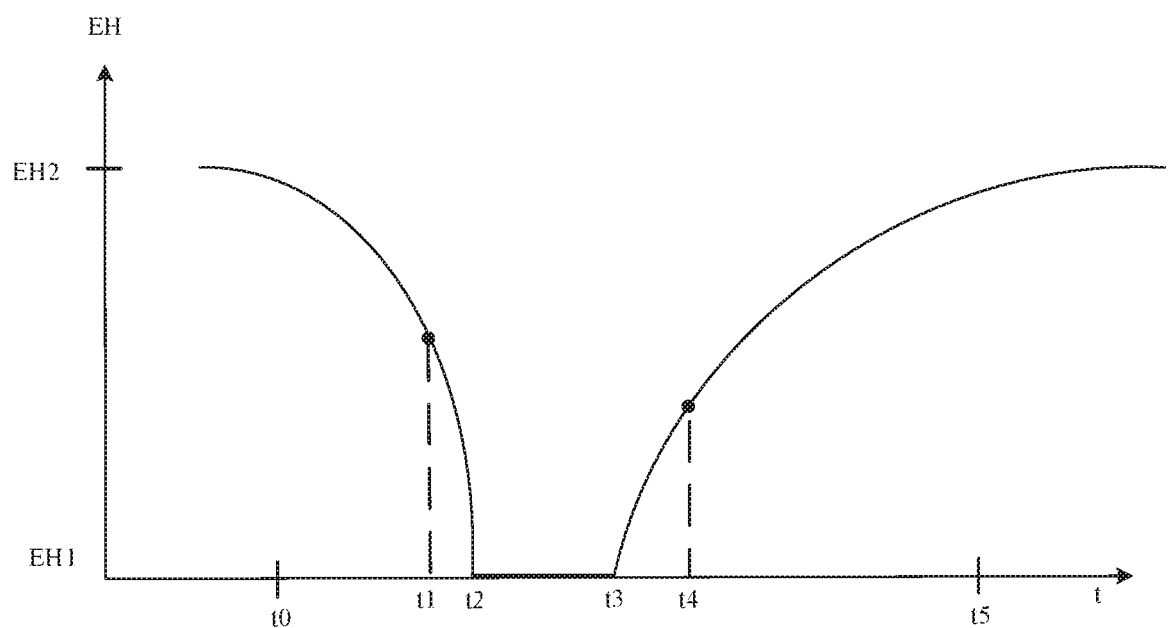
FIG. 4 is a graph showing an illustrative eyelid position as a function of time while a user is viewing a display in accordance with an embodiment.

FIG. 4 is a graph of eyelid position (eye height EH) versus time during an illustrative eye activity such as a blink. At time t0 and earlier times, the eyelid of the user's eye is fully opened (eyelid height EH is equal to EH2). In the example of FIG. 4, the user begins to blink at time t0. System 16 may detect the movement of the eyelid at time t1 (e.g., when eyelid height EH has decreased by a threshold amount such as by 10% or other suitable value). At time t2 of FIG. 4, the user's eye is fully closed (eyelid height EH1 is effectively zero). The user's eye remains closed for the time period between time t2 and t3. At time t3, the user's eyelid begins to open (e.g., the blink is beginning to terminate). System 16 may detect that the user's eyelid is opening at time t4. At time t5, the user's eye is open and eyelid height EH is again EH2. Illustrative opening and/or closing durations (e.g., time t2–t0 and/or t5–t3) may be about 80 ms or more. Illustrative eyelid closure times (e.g., time t3–t2) may be about 75-250 ms. Full eyelid closure may cause more than a 500-fold reduction in the light impinging on the retinas of the user's eyes. The duration of a blink (e.g., the time interval between when eyelids start their closing motion and when they are fully open) ranges from about 200 ms to 500 ms. The light loss due to eyelid closure can be regarded as "passive" suppression; the visual system of the user does not have a role in that part, it simply occurs due to physical occlusion of the light. In addition to the light loss due to eyelid closure, visual sensitivity is actively suppressed by the brain of a user during eye blink events. As a result, there is generally about 100-200 ms during which changes to the operation of display 14 may not be visibly noticeable to a user. Saccadic suppression of visual sensitivity may take place during saccades, which may last about 20-100 ms, and slightly before and after saccades (e.g., 50 ms before and up to 200 ms after each saccade).

Blinks tend to occur at a rate of about 10-20 blinks per minute and may be associated with stronger visual sensitivity loss than saccades, because light is blocked by the user's eyelids during blinks. It may therefore be particularly beneficial to exploit blink-induced visual sensitivity suppression when attempting to mask potentially disruptive display adjustments from a user (e.g., luminance adjustments and other adjustments that could be sensed during a saccade). In general, however, control circuitry 20 may make display operation adjustments during any suitable periods of reduced visual sensitivity associated with eye events (e.g., saccades detected by system 16 and/or blinks detected by system 16).

Figure 5:
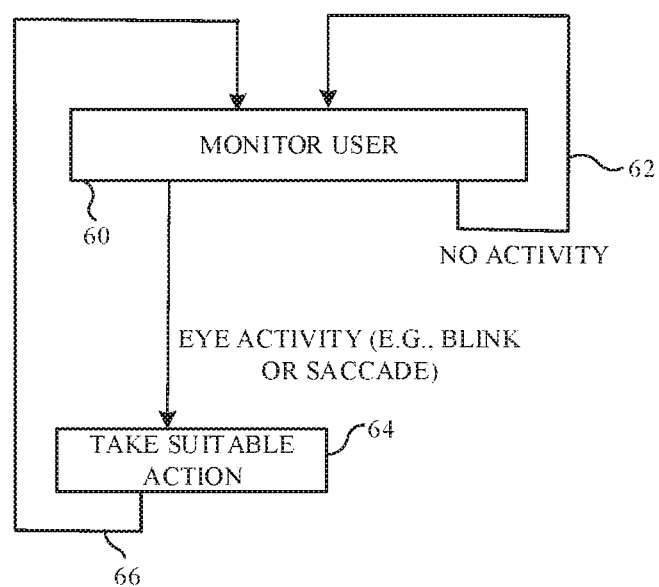
FIG. 5 is a flow chart of illustrative operations involved in using an electronic device with a display and eye monitoring system in accordance with an embodiment.

FIG. 5 is a flow chart of illustrative operations associated with operating device 10.

During the operations of block 60, control circuitry 20 may use eye monitoring system 16 to detect saccades and blinks of the user's eyes. System 16 may detect the time of initiation of saccades and/or the time of initiation of blinks. Eye event duration may also be monitored. For example, system 16 may detect the terminations of saccades and/or blinks. System 16 may have a response time of less than 5 ms, less than 2.5 ms, less than 2 ms, less than 1 ms, or other suitable response time (latency). This response time is generally significantly less than the time periods over which saccadic and blink activity takes place, allowing saccades and blinks to be detected accurately in real time.

If no appropriate eye activity is detected (e.g., no saccade is detected and/or no blink is detected) processing may be continue at block 60, as indicated by line 62. During the operations of block 60, control circuitry 20 may use display 14 to display image content. As image frames are provided to the pixel array formed from pixels P, a corresponding still and/or moving image may be displayed by pixels P.

In response to detection of eye activity, control circuitry 20 may take suitable action. During the operation of block 64, for example, control circuitry 20 may adjust content that is being displayed on display 14 (e.g., by adjusting image data values) and/or may make adjustments to display driver circuitry 46, pixels P, and/or illumination circuitry such as unit 48. The adjustments made during block 64 may tend to be visually noticeable in the absence of a saccade or blink. Accordingly, control circuitry 20 may limit the amount of time of each adjustment of block 64 to a time less than (or just slightly more than) the measured or expected duration of the eye event detected during the operations of block 60.

With one illustrative arrangement, control circuitry 20 may assume that a detected eye event will last for a predetermined duration (e.g., 100 ms) and can plan accordingly so that potentially disruptive display adjustments are performed in less than the predetermined duration (e.g., 100 ms or less) or other appropriate time period (e.g., a time period of 80% of the predetermined duration or a time period of 120% of the predetermined time period). With another illustrative arrangement, control circuitry 20 uses system 16 to detect the commencement of an eye event (e.g., the closing of an eyelid) and to detect the termination of the eye event (e.g., the opening of the eyelid) and may make display adjustments (to hardware and/or image data) accordingly. There may be a non-zero period of time after eyelid opening is detected in which the user's visual sensitivity remains suppressed. This period of time may serve as a grace period during which display operation adjustments may be completed.

After the operations of block 64 are completed, processing may loop back to block 60, as indicated by line 66. During block 64, control circuitry 20 may resume the use of system 16 to monitor for eye activity.

Any suitable adjustments to the operation of display 14 (e.g., display system 40) and device 10 may be made during periods of suppressed visual sensitivity associated with the detected blinks or saccades.

With one illustrative arrangement, control circuitry 20 in device 10 may perform pixel-shifting operations on an image being displayed on pixels P. Pixels P may, for example, be organic light-emitting diode pixels or other pixels that are potentially susceptible to burn-in effects. By shifting the displayed image on display 14 by a number of pixels (e.g., by at least one pixel, at least 2 pixels, at least 5 pixels, at least 10 pixels, 10-25 pixels, at least 20 pixels, fewer than 30 pixels, fewer than 60 pixels, or other suitable pixel shifting value), burn-in effects can be reduced. Pixel shifting operations may be performed by loading an image frame into the array of pixels P that corresponds to an image that is shifted with respect to an image in a previously loaded image frame (e.g., an image frame located before the period of suppressed visual sensitivity) by a given pixel shifting value. The shifted image frame may, for example, be loaded during a time period such as the time period between times t2 and t3 when the user's eyelid is closed or at other time of reduced visual sensitivity. By performing pixel shifting operations during periods of suppressed visual sensitivity associated with detected blinks or saccades, the user will not notice that the pixel shifting operation has taken place. The shifted image location may be maintained following the blink and may be shifted again during a subsequent blink. If desired, scrambled images, images with complementary burn-in correcting pixel values, and/or other images to combat image burn-in effects may be displayed during the periods of suppressed visual sensitivity.

With another illustrative arrangement, circuitry in display 14 may be turned off or display 14 may otherwise be placed in a low power state during periods of suppressed visual sensitivity. For example, an illumination unit such as backlight unit 48 of FIG. 3 may be momentarily powered off during a blink, the process of updating the frames of image data for display 14 by display driver circuitry 46 may be momentarily halted (e.g., frame refreshes may be paused so that the currently displayed frame continues to be displayed without being updated and/or so that the currently displayed frame is repeated, thereby saving computational power), frame updates can be slowed, blank frames (frames with all black pixels) or frames of constant color can be displayed, the brightness of display 14 may be momentarily reduced (e.g., by reducing backlight intensity or adjusting the power supply level associated with pixels P), the overall luminance of the content being displayed on pixels P may be reduced, computer-generated content or other content displayed on display 14 may be displayed at a lower refresh rate and/or resolution, the quantization (number of bits of luminance) for displayed content may be momentarily switched to a coarser scale (fewer bits of luminance resolution), and/or other operations associated with the operation of the circuitry of display 14 and/or the image content being displayed on display 14 may be changed to reduce power consumption.

Display driver circuitry 46 and/or other control circuitry 20 in device 10 may be used in implementing adjustments such as these to reduce power consumption during the periods of suppressed visual sensitivity. After a period of suppressed visual sensitivity is complete (e.g., when a user's blink has finished), normal operation may be resumed (and power consumption can return to its initial higher value). Although power consumption is not reduced during the periods between blinks (or saccades) with this type of arrangement, the periodic reduction of power consumption that occurs during the periods of suppressed visual sensitivity can help reduce the overall power consumption of device 10 over longer periods of time.

In some situations, it may be desirable to make adjustments to the luminance or other properties of displayed images on display 14 in a way that is not obtrusive. For example, when a user transitions from a first environment that is associated with ambient light of a first color (e.g., a high color temperature) to a second environment that is associated with ambient light of a second color (e.g., a low color temperature), it may be desirable to adjust the color cast (e.g., the white point) of image content on display 14 so that the color cast of display 14 tracks the color of the surrounding environment of device 10. To make color cast (white point) adjustments to display 14 less noticeable for a viewer, incremental color cast adjustments can be made during each period of suppressed visual sensitivity. For example, each time a user blinks, the color cast of the image displayed on display 14 can be adjusted towards a desired target color cast by a desired small increment. After sufficient time has passed, all incremental changes will have been made and the image content on display 14 will have a color cast matching the desired target color cast. As another example, incremental luminance changes (e.g., small steps up or down in the brightness of the content displayed on display 14) can be made during the periods of suppressed visual sensitivity. This allows relatively large luminance changes to be implemented without disturbing the user, who may not notice any of the incremental luminance changes because they coincide with the periods of suppressed visual sensitivity. Electro-optical transfer function adjustments (gamma curves) may also be adjusted during periods of suppressed visual sensitivity.

If desired, geometric image transformations may be made during periods of suppressed visual sensitivity. Examples of geometric transformations include shifting transforms, shearing transforms (e.g., to counteract image skew effects due to rolling shutters in image sensors), and homographic transforms (e.g., projective or perspective transforms of the type that may be made to accommodate changes in images overlaid on real-world objects as a user's perspective of the real-world objects changes due to changes in the user's viewing orientation). By allowing perspective and other geometric transforms to be made during periods of suppressed visual sensitivity, situations in which image content on display 14 becomes mismatched with the user's surroundings (e.g., situations with mismatched motion parallax and stereoscopic cues) can be avoided and associated motion sickness and other user discomfort can be avoided. The geometric transforms that are performed on the images for display 14 may be introduced exclusively or primarily during periods of suppressed visual sensitivity so as not to be noticeable to the user. Geometric image transformations may be made by the control circuitry of device 10 during blinks and/or during saccades. Saccades may occur at a higher frequency during blinks, which may provide more opportunities for making these transforms, but geometric image transforms and/or other display operation adjustments may also be made during blinks (where visual sensitivity is further reduced), if desired.

The foregoing is merely illustrative and various modifications can be made to the described embodiments. The foregoing embodiments may be implemented individually or in any combination.

What is claimed is:

1. An electronic device, comprising:
   a display;
   an eye monitoring system; and
   control circuitry that is configured to identify an eye activity using the eye monitoring system, wherein the eye activity comprises an eye blink, wherein the control circuitry is configured to coordinate operation of the display with the eye activity by adjusting operation of the display during the eye activity relative to a time before the eye activity, wherein the control circuitry is configured to reduce image luminance during the eye blink by reducing image data values associated with an image frame displayed during the eye blink relative to an image frame displayed before the eye blink.

2. The electronic device defined in claim 1 wherein the control circuitry is configured to adjust the operation of the display during the eye activity to reduce image burn-in effects on the display.

3. The electronic device defined in claim 1 wherein the control circuitry is configured to implement a pixel shift in an image on the display during the eye activity to reduce the image burn-in effects on the display.

4. The electronic device defined in claim 1 wherein the control circuitry is configured to adjust display brightness during the eye blink, and wherein the display has a first brightness before the eye blink and a second display brightness that is different than the first brightness during the eye blink.

5. The electronic device defined in claim 1 wherein the control circuitry is configured to adjust the operation of the display during the eye blink to reduce power consumption during the eye blink relative to a preceding time that is not during an eye blink.

6. The electronic device defined in claim 1 wherein the control circuitry is configured to adjust the operation of the display by turning off at least some portion of the display during the eye blink.

7. The electronic device defined in claim 1 wherein the control circuitry is configured to adjust operation of the display to reduce power consumption during the eye blink by displaying non-blank image frames outside of the eye blink and displaying at least one blank image frame during the eye blink.

8. The electronic device defined in claim 1 wherein the control circuitry is configured to adjust operation of the display to reduce power consumption by momentarily reducing image resolution during the eye blink.

9. The electronic device defined in claim 1 wherein the control circuitry is configured to adjust operation of the display to reduce power consumption by momentarily reducing an image frame refresh rate for the display during the eye blink.

10. The electronic device defined in claim 1 wherein the control circuitry is configured to:
    display a given image prior to the eye activity; and
    display a version of the given image that has been transformed using a geometrical image transform during the eye activity.

11. The electronic device defined in claim 10 wherein the geometrical image transform comprises a geometrical image transform selected from the group consisting of: a shift and a shear.

12. The electronic device defined in claim 10 wherein the geometrical image transform comprises a geometrical image transform selected from the group consisting of: a projection and a perspective transform.

13. The electronic device defined in claim 1 wherein the control circuitry is configured adjust a color cast of content on the display during the eye blink to relative to a preceding time that is not during an eye blink.

14. The electronic device defined in claim 1 wherein the control circuitry is configured adjust an electro-optical transform for content on the display during the eye blink to relative to a preceding time that is not during an eye blink.

15. An electronic device, comprising:
    a display;
    head-mounted support structures coupled to the display;
    an eye monitoring system; and
    control circuitry that is configured to detect eye blinks using the monitoring system and that is configured to coordinate operation of the display with periods of suppressed visual sensitivity associated with the eye blinks by making display operation adjustments during the eye blinks, wherein the control circuitry is configured to adjust operation of the display to reduce power consumption by momentarily reducing image resolution across an entire image during the eye blink.

16. The electronic device defined in claim 15 wherein the control circuitry is configured to display an image on the display and wherein the control circuitry is configured to make adjustments in overall luminance for the image during the eye blinks.

17. The electronic device defined in claim 15 wherein the control circuitry is configured to display an image on the display and wherein the control circuitry is configured to apply a geometrical image transform to the image during the eye blinks.

18. The electronic device defined in claim 17 wherein the geometrical image transform comprises a perspective transform and wherein the control circuitry is configured to apply the perspective transform to the image in coordination with the eye blinks.

19. A head-mounted display, comprising:
- head-mounted support structures;
- a display supported by the head-mounted support structures, wherein the display is configured to display image content;
- an eye monitoring system; and
- control circuitry that is configured to detect eye blinks using the eye monitoring system and that is configured to coordinate adjustments to the image content with periods of suppressed visual sensitivity associated with the eye blinks, wherein the control circuitry is configured to pixel shift the entire image content during the eye blinks to reduce image burn-in effects on the display.

* * * * *